(12) United States Patent
Minhas et al.

(10) Patent No.: US 11,760,706 B2
(45) Date of Patent: Sep. 19, 2023

(54) NON-AROMATIC COMPOUND REMOVAL SYSTEMS FOR PARA-XYLENE PRODUCTION

(71) Applicant: ExxonMobil Technology and Engineering Company, Annandale, NJ (US)

(72) Inventors: Bhupender S. Minhas, Bridgewater, NJ (US); Jeevan S. Abichandani, Houston, TX (US); Marcus L. H. van Nuland, Rijen (NL); Wai Kit Cheng, Lahat (MY); Chong-Jhoo Wang, Serangoon Central (SG); Robert G. Tinger, Friendswood, TX (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/634,956

(22) PCT Filed: Jul. 2, 2020

(86) PCT No.: PCT/US2020/040615
§ 371 (c)(1),
(2) Date: Feb. 11, 2022

(87) PCT Pub. No.: WO2021/029981
PCT Pub. Date: Feb. 18, 2021

(65) Prior Publication Data
US 2022/0281784 A1    Sep. 8, 2022

Related U.S. Application Data

(60) Provisional application No. 62/886,409, filed on Aug. 14, 2019.

(51) Int. Cl.
*C07C 7/144* (2006.01)
*C07C 7/10* (2006.01)
(Continued)

(52) U.S. Cl.
CPC ............ *C07C 7/144* (2013.01); *B01D 61/007* (2013.01); *C07C 7/005* (2013.01); *B01D 2317/025* (2013.01)

(58) Field of Classification Search
None
See application file for complete search history.

(56) References Cited

U.S. PATENT DOCUMENTS 6,187,987 B1    2/2001   Chin et al.
2008/0200696 A1  8/2008   Miller et al.
(Continued)

FOREIGN PATENT DOCUMENTS

JP    2002302461 A    10/2022
WO    2017105922 A1    6/2017

OTHER PUBLICATIONS

PCT/US2020/040615 Written Opinion dated Jan. 17, 2022.
(Continued)

*Primary Examiner* — Tam M Nguyen
(74) *Attorney, Agent, or Firm* — Shook, Hardy & Bacon L.L.P.

(57) ABSTRACT

Selective removal of non-aromatic hydrocarbons from a xylene isomerization process for para-xylene production is accomplished using a membrane unit positioned within a xylene recovery loop. The membrane unit may include a one-stage or multi-stage (e.g., two-stage) membrane system and may be configured to separate a membrane unit product stream from a non-aromatics rich stream, which can be removed from the xylene recovery loop. The membrane unit
(Continued)

may have a xylene permeance of about 60 gm/m2/hr/psi and a xylene to non-aromatic permeance ratio of about 15.

9 Claims, 5 Drawing Sheets

(51) Int. Cl.
    *B01D 61/00*     (2006.01)
    *C07C 7/00*     (2006.01)

(56) References Cited

U.S. PATENT DOCUMENTS

| | | | |
|---|---|---|---|
| 2009/0149686 A1 | 6/2009 | Leflaive et al. | |
| 2015/0376088 A1* | 12/2015 | Molinier | C07C 7/13 |
| | | | 585/314 |
| 2016/0046544 A1 | 2/2016 | Moliner et al. | |
| 2016/0318827 A1* | 11/2016 | Tinger | C07C 5/2729 |
| 2017/0137350 A1 | 5/2017 | Weiss et al. | |
| 2018/0002253 A1* | 1/2018 | Dorsi | C07C 7/12 |
| 2018/0122021 A1* | 5/2018 | Horn | G06Q 10/06316 |
| 2022/0033721 A1* | 2/2022 | Koseoglu | C10G 29/00 |
| 2022/0220397 A1* | 7/2022 | Koseoglu | C10G 11/18 |
| 2022/0281784 A1* | 9/2022 | Minhas | C07C 7/005 |

OTHER PUBLICATIONS

Office Action from China Patent Office for Invention No. 202080056690.6 dated Jun. 1, 2023 (8 pages total—6 pages of Office Action, 2 pages of translation).

* cited by examiner

NON-AROMATIC COMPOUND REMOVAL SYSTEMS FOR PARA-XYLENE PRODUCTION

CROSS-REFERENCE TO RELATED APPLICATIONS

This application is the 35 USC § 371 National Stage Application of PCT Application Number PCT/US2020/040615, filed on Jul. 2, 2020, which claims the benefit of U.S. Provisional Application No. 62/886,409, filed on Aug. 14, 2019, the entire contents of both of which are incorporated herein by reference.

FIELD OF THE INVENTION

The present disclosure is directed to non-aromatic compound removal systems and, more particularly, to systems and methods for removing non-aromatic compounds from a xylene isomerization process for para-xylene production.

BACKGROUND

Of the xylene isomers, para-xylene is by far the most important for commercial applications, particularly as a feedstock for production of many industrial chemicals. Current xylene isomerization processes aim to produce and separate the para-xylene isomer from the meta- and ortho-xylene isomers using a variety of methods. Typically, these processes involve the use of a feed stock, for example a reformate, that includes mixed xylenes and non-aromatic compounds (or non-aromatics).

After separation of para-xylene, the unconverted meta- and ortho-xylenes are recycled back to the isomerization reactor, along with the non-aromatic compounds. The concentration of non-aromatics continues to increase within the recycle loop as fresh feed containing non-aromatics continues to be added to the isomerization reactor feed and para-xylene continues to be removed from the recycle loop. Due to this, non-aromatic concentration continues to build in the recycle loop negatively affecting the para-xylene yield, and overall process efficiency and capacity.

In current commercial practice, this increase in concentration of non-aromatic compounds is controlled by purging a certain amount of the recycle stream, which results in the loss of xylenes along with the non-aromatics. In some instances, where a continuous purge is insufficient to control non-aromatic compound build-up, the entire recycle inventory is periodically dumped.

Accordingly, there is need for improved systems for selectively removing non-aromatic compounds from a xylene isomerization process for para-xylene production to improve yield, and overall process efficiency, and capacity. The disclosed systems and methods are directed to overcoming these and other considerations.

SUMMARY

In various aspects, systems and methods for removing non-aromatic compounds from a xylene isomerization process for para-xylene production are provided. A non-aromatic compound removal system may include one or more components of a, a xylene recovery loop, which may include a xylene splitter, a para-xylene recovery unit, an isomerization unit, a deheptanizer unit, and a clay treater, and a membrane unit (e.g., a one-stage or multi-stage system) strategically positioned within the xylene recovery loop depending on the application. Regardless of its position within the xylene recovery unit, the membrane unit may be configured to preferentially permeate xylenes such that it allows other molecules (e.g., non-aromatics) to permeate more slowly than xylene if it allows those other molecules to permeate at all. In this manner, the membrane unit separates a non-aromatics rich stream from other streams within the xylene recovery loop so that the non-aromatics rich stream can be removed while the xylene recovery loop efficiently and effectively (e.g., at a higher yield and/or capacity level for xylene-containing streams, which can occupy the space of the removed non-aromatics) processes the remaining streams and/or new reformate stream(s). By removing the non-aromatics rich stream, the xylene recovery loop can operate at a higher yield, more efficiently and effectively, with a higher capacity for xylene-containing streams, and lower cost. It can also operate continuously without requiring stoppage of the xylene isomerization process to dump contents of the xylene recovery loop in an effort to purge the non-aromatics. The membrane unit may be configured to present a xylene permeance of between 5-150 gm/m$^2$/hr/psi (e.g., between about 40-80 gm/m$^2$/hr/psi in some embodiments and about 60 gm/m$^2$/hr/psi in other embodiments) and a xylene to non-aromatic permeance ratio of 3-70 (e.g., between about 10-25 in some embodiments and about 15 in other embodiments). It is advantageous to maximize both the xylene permeance and xylene to non-aromatic permeance ratio to improve performance, though doing so requires balancing the two values as the xylene permeance and xylene to non-aromatic permeance ratio are inversely related (e.g., increasing the value of one decreases the other). Increasing the xylene permeance helps to reduce the required surface area for the membrane unit. Increasing the xylene to non-aromatic permeance ratio provides cleaner separation between xylenes and non-aromatics (e.g., at a ratio of 15, xylene is permeating through the membrane 15 times faster than non-aromatics). The inputs, outputs, and efficiency of the membrane unit vary based on its position within the xylene recovery loop.

For example, in one aspect, the membrane unit may be positioned upstream of the xylene splitter such that it is configured to receive a reformate stock stream and produce a non-aromatics rich stream and a membrane unit product stream. In this configuration (i.e., with the membrane unit positioned upstream of the xylene splitter), the xylene splitter may be configured to receive the membrane unit product stream and produce a mixed xylene stream, which may include para-xylene, ortho-xylene, and meta-xylene. Other components (e.g., the para-xylene recovery unit, isomerization unit, deheptanizer unit, and clay treater) of the xylene recovery loop may be configured to receive and process the mixed xylene stream, which may include processing the mixed xylene stream in the para-xylene recovery unit to produce a para-xylene rich stream and a para-xylene lean stream, processing the para-xylene lean stream in the isomerization unit to produce an isomerization unit product stream, feeding the isomerization unit product stream into the deheptanizer unit to produce a xylene rich stream, processing the xylene rich stream through a clay treater to produce a clay treated stream, and feeding the clay treated stream back into the xylene splitter for recirculation within the xylene recovery loop.

In another exemplary aspect, the membrane unit may be repositioned downstream of the xylene splitter and upstream of the remaining components of the xylene recovery loop. In this configuration, the xylene splitter may be configured to receive a reformate stock stream and produce a mixed xylene stream, which may include para-xylene, ortho-xylene, and meta-xylene. The membrane unit may be in direct fluid communication with the xylene splitter such that it is configured to receive the mixed xylene stream and produce a non-aromatics rich stream and a membrane unit product stream. The para-xylene recovery unit may be in direct fluid communication with the membrane unit such that it is configured to receive the membrane unit product stream and produce a para-xylene lean stream. The isomerization unit may be in direct fluid communication with the para-xylene recovery unit and configured to process the para-xylene lean stream to produce an isomerization unit product stream, which is in turn fed into the deheptanizer unit. The deheptanizer unit may be in direct fluid communication with the isomerization unit and configured to produce a xylene rich stream, which can then be processed through the clay treater. The clay treater may be in direct fluid communication with the deheptanizer unit and configured to produce a clay treated stream, which can then be fed into the xylene splitter for recirculation within the xylene recovery loop.

In a further exemplary aspect, the membrane unit may be repositioned downstream of the xylene splitter and between the para-xylene recovery unit and the deheptanizer unit of the xylene recovery loop. In this configuration, the xylene splitter may be configured to receive a reformate stock stream and produce a mixed xylene stream, which may include para-xylene, ortho-xylene, and meta-xylene. The para-xylene recovery unit may be in direct fluid communication with the xylene splitter and configured to receive the mixed xylene stream from the xylene splitter and produce a para-xylene lean stream. The membrane unit may be in direct fluid communication with the para-xylene recovery unit and configured to receive the para-xylene lean stream and produce a non-aromatics rich stream and a membrane unit product stream. Because the membrane unit may be configured to receive the para-xylene lean stream rather than a reformate stream or mixed xylene stream, it may operate more efficiently in this position. The deheptanizer unit may be in fluid communication with the para-xylene recovery unit (e.g., by way of the membrane unit and, optionally, an isomerization unit) and configured to produce a hydrocarbon stream. Optionally, a clay treater may be in direct fluid communication with the deheptanizer unit and the xylene splitter such that it is configured to receive the xylene rich stream from the deheptanizer unit and produce a clay treated stream, which can then be fed to the xylene splitter for recirculation within the xylene recovery loop.

In yet another exemplary aspect, the membrane unit may be repositioned downstream of the deheptanizer unit of the xylene recovery loop. In this configuration, the xylene splitter may be configured to receive a reformate stock stream and produce a mixed xylene stream, which may include para-xylene, ortho-xylene, and meta-xylene. The para-xylene recovery unit may be in direct fluid communication with the xylene splitter and configured to receive the mixed xylene stream from the xylene splitter and produce a para-xylene lean stream. The deheptanizer unit may be in fluid communication with the para-xylene recovery unit (e.g., directly or, optionally, indirectly by way of an isomerization unit) and configured to produce a hydrocarbon stream. The membrane unit may be in direct fluid communication with the deheptanizer unit and configured to receive the hydrocarbon stream and produce a non-aromatics rich stream and a membrane unit product stream. Optionally, a clay treater may be in direct fluid communication with the deheptanizer unit and the xylene splitter such that it is configured to receive the xylene rich stream from the deheptanizer unit and produce a clay treated stream, which can then be fed to the xylene splitter for recirculation within the xylene recovery loop.

DETAILED DESCRIPTION

Figure 1:
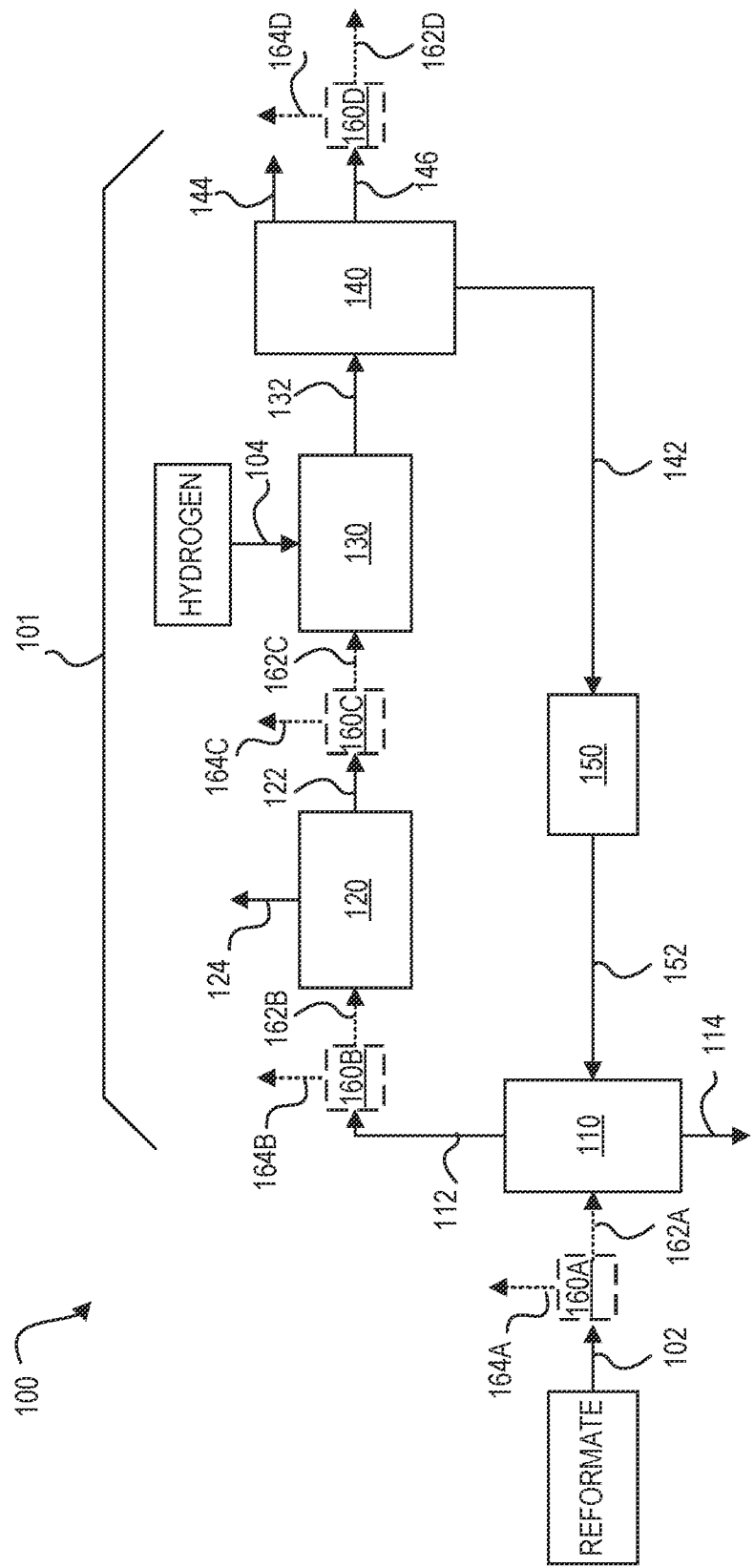
FIG. 1 is a diagrammatic illustration of an exemplary disclosed non-aromatic compound removal system with multiple configurations.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the embodiments, terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Ranges can be expressed herein as from "about" or "approximately" one particular value and/or to "about" or "approximately" another particular value. When such a range is expressed, another embodiment includes from the one particular value and/or to the other particular value.

The term "aromatic" is used herein to designate a hydrocarbon-based organic compound containing at least one aromatic ring. The term "non-aromatic" is used herein to designate a hydrocarbon compound having no aromatic nucleus. The term "mixed xylene" is used herein to designate a mixture comprising meta-xylene, ortho-xylene, and para-xylene.

It is also to be understood that the mention of one or more method steps does not preclude the presence of additional method steps or intervening method steps between those steps expressly identified, nor is the disclosure limited by the order in which the method steps are expressly identified. Similarly, it is also to be understood that the mention of one or more components in a system does not preclude the presence of additional components or intervening components between those components expressly identified, nor is the disclosure limited by the order in which the components are expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As described above, current xylene isomerization processes for para-xylene production use feed stocks that contain certain amounts of non-aromatic compounds. These non-aromatics are recycled back to an isomerization reactor along with the unconverted ortho- and meta-xylenes after separation of para-xylene. The concentration of non-aromatics within the recycle loop increases as fresh feed stock containing non-aromatics continues to be added to the isomerization reactor feed. The continual build-up of non-aromatics in the system results in decreased recycle loop capacity for xylene-containing streams (e.g., due to the space occupied by the non-aromatics within the recycle loop), efficiency, and para-xylene yield. Certain amounts of recycle streams must therefore be periodically purged or even completely dumped, leading to the loss of xylenes along with the non-aromatics.

Disclosed herein, therefore, are systems and methods for selectively removing non-aromatic compounds from a xylene isomerization process for para-xylene production by employing a membrane unit in one or more positions within the system. The membrane unit continually removes non-aromatics from the process, minimizing/eliminating the need for purging or dumping of any process stream. To accomplish this, the membrane unit may preferentially permeate xylene while either not permeating other molecules (e.g., non-aromatics) or permeating those other molecules more slowly in order to separate the xylenes from the other molecules. This separation is not accomplished by filtering based on size of the molecules, but rather by permitting xylene to dissolve and diffuse through the membrane unit preferentially over non-aromatics.

References will now be made in detail to example embodiments of the disclosed technology, examples of which are illustrated in the accompanying drawings and disclosed herein. Wherever convenient, the same reference numbers will be used throughout the drawings to refer to the same or like parts.

FIG. 1 illustrates a non-aromatic compound removal system 100 having multiple in-use configurations for removing non-aromatic compounds from a xylene isomerization process for para-xylene production in accordance with some embodiments. As shown, the system 100 may include a xylene recovery loop 101, which may include one or more components of a xylene splitter 110, a para-xylene recovery unit 120, an isomerization unit 130, a deheptanizer unit 140, and a clay treater 150, and at least one of a membrane unit 160A, 160B, 160C, and 160D positioned as shown within the system 100. For example, the membrane unit 160A may be positioned upstream of the xylene splitter 110 in a first configuration of the system 100, the membrane unit 160B may be positioned between the xylene splitter 110 and the para-xylene recovery unit 120 in a second configuration of the system 100, the membrane unit 160C may be positioned between the para-xylene recovery unit 120 and the isomerization unit 130 in a third configuration of the system 100, and the membrane unit 160D may be positioned downstream of the deheptanizer unit 140 in a fourth configuration of the system 100, as described in more detail below. In some embodiments, a single membrane unit or multiple membrane units 160A-D may be used within the system 100. The components of the system 100 are in fluid communication with one another, directly or indirectly, and collectively configured to receive a reformate stream and produce a para-xylene rich stream, a non-aromatics rich stream, and a heavier hydrocarbon stream that may include C9 and C10 hydrocarbons.

The xylene splitter 110 may be in direct fluid communication with one or more of a reformate stream, the membrane unit 160A, the membrane unit 160B, the para-xylene recovery unit 120, and the clay treater 150 such that it is configured to receive, directly or indirectly, a reformate stock stream 102 (e.g., from a source external to the system 100) or a membrane unit product stream 162A (e.g., from membrane unit 160A) and to output a xylene rich stream 112 and a heavier hydrocarbon stream 114 that may include C9 and C10 hydrocarbons. The xylene splitter 110 may include a fractional distillation column, selective sorption unit, or other technology known in the art.

Positioned downstream of the xylene splitter 110 within the xylene recovery loop 101, the para-xylene recovery unit 120 may be in direct fluid communication with one or more of the xylene splitter 110, the membrane unit 160B, the membrane unit 160C, the isomerization unit 130, and the deheptanizer unit 140 such that it is configured to receive, directly or indirectly, the mixed xylene stream 112 (e.g., from the xylene splitter 110) or a membrane unit product stream 162B (e.g., from membrane unit 160B) and to output a para-xylene lean stream 122 and a para-xylene rich stream 124. The para-xylene recovery unit 120 may include one or more of any of the para-xylene recovery units known in the art, including, for example, a crystallization unit, an adsorption unit (such as a PAREX™ unit or an ELUXYL™ unit), a reactive separation unit, a membrane separation unit, an extraction unit, a distillation unit, an extractive distillation unit, a fractionation unit, a simulated moving bed type of recovery unit, or any combination thereof.

Positioned further downstream within the xylene recovery loop 101, the isomerization unit 130 may be in direct fluid communication with one or more of the para-xylene recovery unit 120, the membrane unit 160C, and the deheptanizer unit 140 such that it is configured to receive, directly or indirectly, a hydrogen stream 104 (e.g., from a source external to the system 100) and the para-xylene lean stream 122 (e.g., from the para-xylene recovery unit 120) or a membrane unit product stream 162C (e.g., from membrane unit 160C), and to output an isomerization unit product stream 132. The isomerization unit 130 may produce equilibrium xylene ratios of approximately about 50% by weight meta-xylene, about 26% by weight ortho-xylene, and about 24% by weight para-xylene. In other embodiments, the equilibrium xylene ratio of para-xylene may be under 24%, and the ratios for meta-xylene and ortho-xylene would be proportionally higher. The isomerization unit 130 may also crack certain hydrocarbons to form lighter molecules, categorized as fuel gas, as well as certain aromatics. The isomerization unit 130 may be any type of isomerization unit known in the art, including, for example, a unit comprising a catalyst for adequate xylene conversion.

Positioned downstream of the isomerization unit 130 within the xylene recovery loop 101, the deheptanizer unit 140 may be in direct fluid communication with one or more of the para-xylene recovery unit 120, the membrane unit 160C, the isomerization unit 130, and the clay treater 150 such that it is configured to receive, directly or indirectly, the para-xylene lean stream 122 (e.g., from the para-xylene recovery unit 120), the membrane unit product stream 162C (e.g., from membrane unit 160C), or the isomerization unit product stream 132 (e.g., from the isomerization unit 130) and to output a xylene rich stream 142, a fuel gas stream 144, and a hydrocarbon stream 146 that may include C6 aromatic compounds, C7 aromatic compounds, and non-aromatic compounds. The deheptanizer unit 140 may be any type of deheptanizer known in the art, including, for example, a trayed distillation column.

Positioned downstream of the deheptanizer unit within the xylene recovery loop 101, the clay treater 150 may be in direct fluid communication with one or more of the deheptanizer unit 140 and the xylene splitter 110 such that it is configured to receive, directly or indirectly, the xylene rich stream 142 (e.g., from the deheptanizer unit 140) and to output a clay treated stream 152, which may be fed back into the xylene splitter 110. The clay treater 150, which may be any type of clay treater known in the art, may be used for reacting olefin molecules in the xylene rich stream 142.

One or more membrane units 160A, 160B, 160C, 160D may be positioned within the system 100 as shown in FIG. 1, and the position of the membrane unit(s) 160A, 160B, 160C, 160D within the system 100 affects the functions of the membrane unit(s) 160A, 160B, 160C, 160D and other components within the system 100 as described in more detail for each embodiment below. Regardless of its position within the system 100, the membrane unit(s) 160A, 160B, 160C, 160D may each be configured to receive and generate process streams (e.g., via one or more inlet ports and one or more outlet ports). The membrane unit(s) 160A, 160B, 160C, 160D may each be further configured to receive a process stream at an inlet pressure of between about 300-1500 psig using a pump the process stream containing between about 1-25% non-aromatics, mixed xylenes, C6 aromatic compounds, and C7 aromatic compounds. In some embodiments, the inlet pressure may be constant and approximately between 200 to 2000 psig. In other embodiments, the inlet pressure may be constant and approximately 800 psig. In further embodiments, the process stream may contain approximately 16.5% non-aromatics, mixed xylenes, C6 aromatic compounds, and C7 aromatic compounds, though this percentage may vary. Functionally, the membrane unit(s) 160A, 160B, 160C, 160D may each have a xylene permeance of between 5-150 gm/m$^2$/hr/psi (e.g., between approximately 40-80 gm/m$^2$/hr/psi in some embodiments and approximately 60 gm/m$^2$/hr/psi in other embodiments) and a xylene to non-aromatic permeance ratio of 3-70 (e.g., between about 10-25 in some embodiments and about 15 in other embodiments). It is advantageous to maximize both the xylene permeance and xylene to non-aromatic permeance ratio to improve performance, though doing so requires balancing the two values as the xylene permeance and xylene to non-aromatic permeance ratio are inverse to one another (e.g., increasing the value of one decreases the other) and makes the membrane unit more difficult to construct. Increasing the xylene permeance reduces the membrane surface area required. Increasing the xylene to non-aromatic permeance ratio provides cleaner separation between xylenes and non-aromatics (e.g., at a ratio of 15, xylene is permeating through the membrane 15 times faster than non-aromatics). The inputs, outputs, and efficiency of the membrane unit vary based on its position within the xylene recovery loop.

Structurally, membrane unit(s) 160A, 160B, 160C, 160D may each include a one-stage or multi-stage (e.g., two-stage) membrane system. A one-stage system may be configured to remove approximately 50% of non-aromatics present in an inlet stream while losing approximately 10% of aromatics present in the inlet stream, the aromatics comprising mixed xylenes. A two-stage or other multi-stage membrane system may remove approximately 50% of non-aromatics present in an inlet stream while reducing the loss of aromatics to half of that of single stage membrane system. Adding stages to the membrane unit(s) increases purity of the xylenes that it preferably permeates, though it costs more to construct and maintain.

The structure and materials of the membrane(s) making up the membrane unit(s) 160A, 160B, 160C, 160D may vary. Similarly, like the structure and materials of the membrane(s), the position of the membrane unit(s) 160A, 160B, 160C, 160D within the xylene recovery loop 101 may impact its performance and overall performance of the system 100. Functionalities of the membrane unit(s) 160A, 160B, 160C, 160D at their respective positions are described in more detail below.

Membrane Unit 160A

In one embodiment of system 100, the membrane unit 160A may be positioned upstream of the xylene splitter 110 such that it is configured to receive the reformate stock stream 102 (e.g., from a source external to the system 100) and in direct fluid communication with the xylene splitter 110. The reformate stock stream 102 may include non-aromatic compounds, mixed xylenes, C6 aromatic compounds, and C7 aromatic compounds. In this position, the membrane unit 160A may be further configured to produce the membrane unit product stream 162A and the non-aromatics rich stream 164A.

In this configuration of the system 100, the xylene splitter 110 may be in direct fluid communication with the membrane unit 160A and configured to receive (e.g., via one or more inlet ports) the membrane unit product stream 162A and produce and expel (e.g., via one or more outlet ports) the mixed xylene stream 112 and the heavier hydrocarbon stream 114 that may include C9 and C10 hydrocarbons.

The para-xylene recovery unit 120 may be in direct fluid communication with the xylene splitter 110 and configured to receive the mixed xylene stream 112 and produce the para-xylene lean stream 122 and the para-xylene rich stream 124. The para-xylene recovery unit 120 may be configured to direct the para-xylene rich stream 124 out of the system 100 as a product and direct the para-xylene lean stream 122, which includes mixed xylenes, downstream within the system 100 for further processing.

The isomerization unit 130 may be in direct fluid communication with the para-xylene recovery unit 120 and the deheptanizer unit 140 such that it is configured to receive the para-xylene lean stream 122 from the para-xylene recovery unit 120 and the hydrogen stream 104 from a hydrogen source (not shown) outside of the system 100 and produce the isomerization unit product stream 132. The isomerization unit 130 may be configured to direct the isomerization unit product stream 132 to the deheptanizer unit 140.

The deheptanizer unit 140 may be in direct fluid communication with the isomerization unit 130 and the clay treater 150 such that it is configured to receive the isomerization unit product stream 132 from the isomerization unit 130 and produce the xylene rich stream 142, the fuel gas stream 144, and the hydrocarbon stream 146. The hydrocarbon stream 146 may include C6 aromatic compounds, C7 aromatic compounds, and non-aromatic compounds. The deheptanizer unit 140 may be configured to direct the xylene rich stream 142 to the clay treater 150 and direct the fuel gas stream 144 and the hydrocarbon stream 146 outside of the system 100.

The clay treater 150 may be in direct fluid communication with the deheptanizer unit 140 and the xylene splitter 110 such that it is configured to receive the xylene rich stream 142 from the deheptanizer unit 140 and produce the clay treated stream 152, which may be fed back into the xylene splitter 110.

Membrane Unit 160B

In one embodiment of system 100, the membrane unit 160B may be positioned between the xylene splitter 110 and the para-xylene recovery unit 120 such that it is configured to receive the mixed xylene stream 112 (e.g., from the xylene splitter 110) and in direct fluid communication with the xylene splitter 110. In this position, the membrane unit 160B may be further configured to produce the membrane unit product stream 162B and the non-aromatics rich stream 164B.

In this configuration of the system 100, the xylene splitter 110 may be in direct fluid communication with the membrane unit 160B and configured to receive (e.g., via one or more inlet ports) the reformate stock stream 102 and produce and expel (e.g., via one or more outlet ports) the mixed xylene stream 112 and the heavier hydrocarbon stream 114 that may include C9 and C10 hydrocarbons.

The para-xylene recovery unit 120 may be in direct fluid communication with the membrane unit 160B and configured to receive the membrane unit product stream 162B and produce the para-xylene lean stream 122 and the para-xylene rich stream 124. The para-xylene recovery unit 120 may be configured to direct the para-xylene rich stream 124 out of the system 100 as a product and direct the para-xylene lean stream 122, which includes mixed xylenes, downstream within the system 100 for further processing.

The isomerization unit 130, the deheptanizer unit 140, and the clay treater 150 may be configured to operate in the same or similar fashion as previously described in the embodiment of membrane unit 160A.

Membrane Unit 160C

In one embodiment of system 100, the membrane unit 160C may be positioned between the para-xylene recovery unit 120 and the isomerization unit 130 such that it is configured to receive the para-xylene lean stream 122 (e.g., from the para-xylene recovery unit 120) and in direct fluid communication with the para-xylene recovery unit 120. In this position, the membrane unit 160C may be further configured to produce the membrane unit product stream 162C and the non-aromatics rich stream 164C.

In this configuration of the system 100, the xylene splitter 110 may be in direct fluid communication with the para-xylene recovery unit 120 and configured to receive (e.g., via one or more inlet ports) the reformate stock stream 102 and produce and expel (e.g., via one or more outlet ports) the mixed xylene stream 112 and the heavier hydrocarbon stream 114 that may include C9 and C10 hydrocarbons.

The para-xylene recovery unit 120 may be in direct fluid communication with the xylene splitter 110 and configured to receive the mixed xylene stream 112 and produce a para-xylene lean stream 122 and a para-xylene rich stream 124. The para-xylene recovery unit 120 may be configured to direct the para-xylene rich stream 124 out of the system 100 as a product and direct the para-xylene lean stream 122, which includes mixed xylenes, downstream within the system 100 for further processing.

The isomerization unit 130 may be in direct fluid communication with the membrane unit 160C such that it is configured to receive the membrane unit product stream 162C and the hydrogen stream 104 from a hydrogen source (not shown) outside of the system 100 and produce the isomerization unit product stream 132. The isomerization unit 130 may be configured to direct the isomerization unit product stream 132 to the deheptanizer unit 140.

The deheptanizer unit 140 and the clay treater 150 may be configured to operate in the same or similar fashion as previously described in the embodiment of membrane unit 160A.

Membrane Unit 160D

In one embodiment of system 100, the membrane unit 160D may be positioned downstream of the deheptanizer unit 140 such that it is configured to receive the hydrocarbon stream 146 (e.g., from the deheptanizer unit 140) and in direct fluid communication with the deheptanizer unit 140. In this position, the membrane unit 160D may be further configured to produce the membrane unit product stream 162D and the non-aromatics rich stream 164D.

In this configuration of the system 100, the xylene splitter 110 may be configured to operate in the same or similar fashion as previously described in the embodiment of membrane unit 160C.

The para-xylene recovery unit 120 and the isomerization unit 130 may be configured to operate in the same or similar fashion as previously described in the embodiment of membrane unit 160A.

The deheptanizer unit 140 may be in direct fluid communication with the isomerization unit 130, the membrane unit 160D, and the clay treater 150 such that it is configured to receive the isomerization unit product stream 132 from the isomerization unit 130 and produce the xylene rich stream 142, the fuel gas stream 144, and the hydrocarbon stream 146. The hydrocarbon stream 146 may include C6 aromatic compounds, C7 aromatic compounds, and non-aromatic compounds. The deheptanizer unit 140 may be configured to direct the xylene rich stream 142 to the clay treater 150, the fuel gas stream 144 outside of the system 100, and the hydrocarbon stream 146 to the membrane unit 160D.

The clay treater 150 may be configured to operate in the same or similar fashion as previously described in the embodiment of membrane unit 160A.

Described below are example methods for removing non-aromatic compounds from a xylene isomerization process for para-xylene production in accordance with example embodiments. These methods may be used in conjunction with the system of FIG. 1 in multiple configurations.

Figure 2:
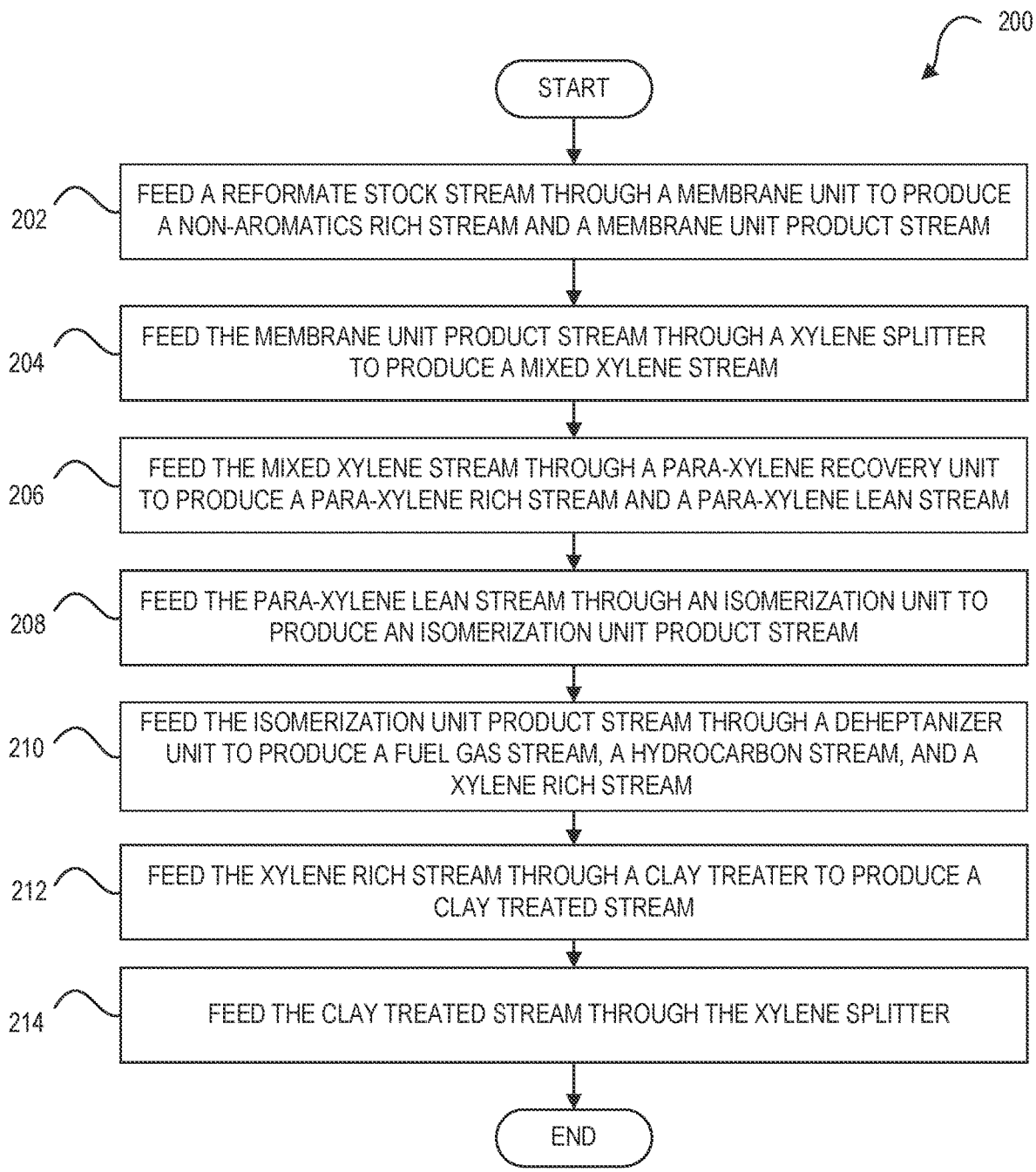
FIG. 2 is a flow chart illustrating a method for removing non-aromatic compounds from a xylene isomerization process for para-xylene production in accordance with an example embodiment, which may be used in conjunction with the system of FIG. 1 in a first configuration.

FIG. 2 illustrates a method 200 for removing non-aromatic compounds from a xylene isomerization process for para-xylene production with the membrane unit 160A in the first position. As shown in FIG. 2, the method 200 may commence at operation 202 with feeding the reformate stock stream 102 through the membrane unit 160A, which may be configured to produce the membrane unit product stream 162A and the non-aromatics rich stream 164A. At operation 204, 160A may feed the membrane unit product stream 162A to the xylene splitter 110, which may be configured to produce the mixed xylene stream 112 and the heavier hydrocarbon stream 114. At operation 206, the xylene splitter 110 may feed the mixed xylene stream 112 to the para-xylene recovery unit 120, which may be configured to produce the para-xylene lean stream 122 and the para-xylene rich stream 124. At operation 208, the para-xylene recovery unit 120 may feed the para-xylene lean stream 122 to the isomerization unit 130, which may be configured to produce the isomerization unit product stream 132. At operation 210, the isomerization unit 130 may feed the isomerization unit product stream 132 to the deheptanizer unit 140, which may be configured to produce the xylene rich stream 142, the fuel gas stream 144, and the hydrocarbon stream 146. At operation 212, the deheptanizer unit 140 may feed the xylene rich stream 142 to the clay treater 150, which may be configured to produce the clay treated stream 152. At operation 214, the clay treater 150 may feed the clay treated stream 152 to the xylene splitter 110 for recirculation within the xylene recover loop 101. Alternatively, the clay treated stream 152 may be outputted from the system 100 rather than recirculated through the xylene recovery loop 101. It should be noted that method 200 may be stopped at any operational step with the output stream(s) of that step being sold to another processing plant.

Figure 3:
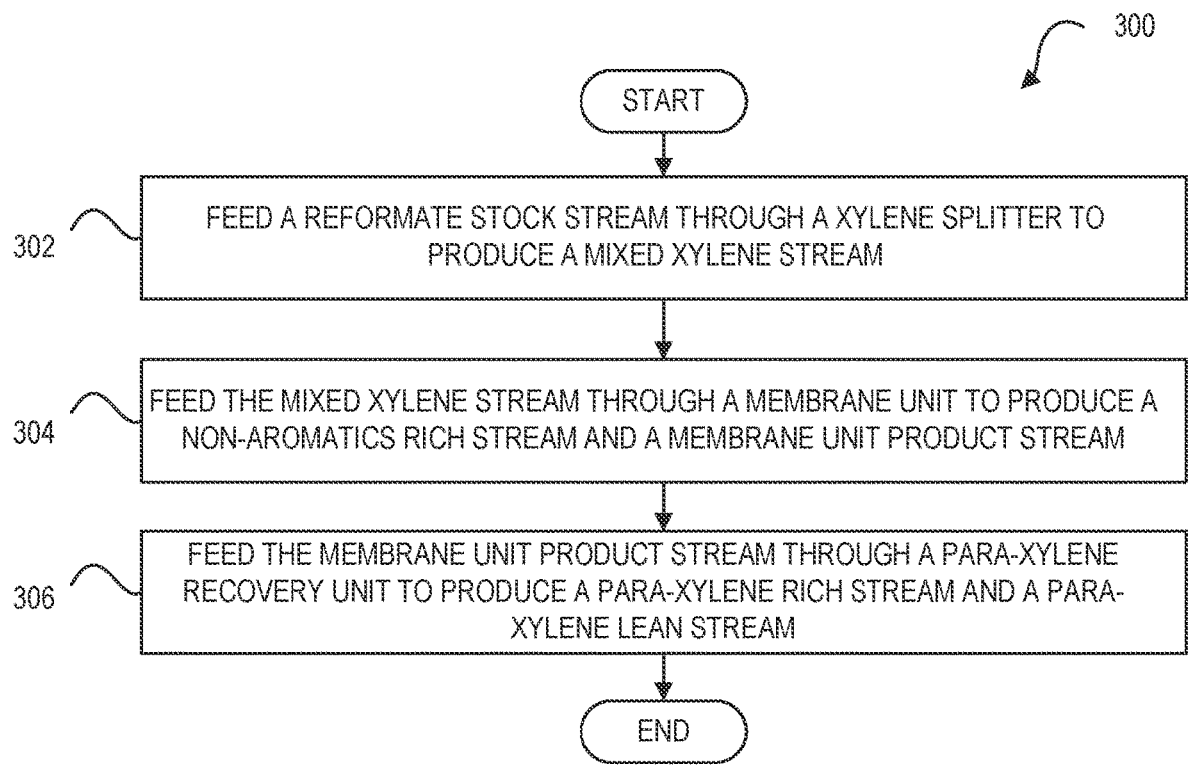
FIG. 3 is a flow chart illustrating a method for removing non-aromatic compounds from a xylene isomerization process for para-xylene production in accordance with an example embodiment, which may be used in conjunction with the system of FIG. 1 in a second configuration.

FIG. 3 illustrates a method 300 for removing non-aromatic compounds from a xylene isomerization process for para-xylene production with the membrane unit 160B in the second position. As shown in FIG. 3, the method 300 may commence at operation 302 with feeding the reformate stock stream 102 through the xylene splitter 110, which may be configured to produce the mixed xylene stream 112 and the heavier hydrocarbon stream 114. At operation 304, the xylene splitter 110 may feed the mixed xylene stream 112 to the membrane unit 160B, which may be configured to produce the membrane unit product stream 162B and the non-aromatics rich stream 164B. At operation 306, the membrane unit 160B may feed the membrane unit product stream 162B to the para-xylene recovery unit 120, which may be configured to produce the para-xylene lean stream 122 and the para-xylene rich stream 124. At this point, the method 300 may be stopped with the output para-xylene lean stream 122 and the para-xylene rich stream 124 being sold to another processing plant. Alternatively, although not shown, the method 300 may proceed with directing one or more of those output streams for further processing to one or more of the isomerization unit 130, the deheptanizer 140, the clay treater 150, and/or one or more additional membrane units 160C, 160D.

Figure 4:
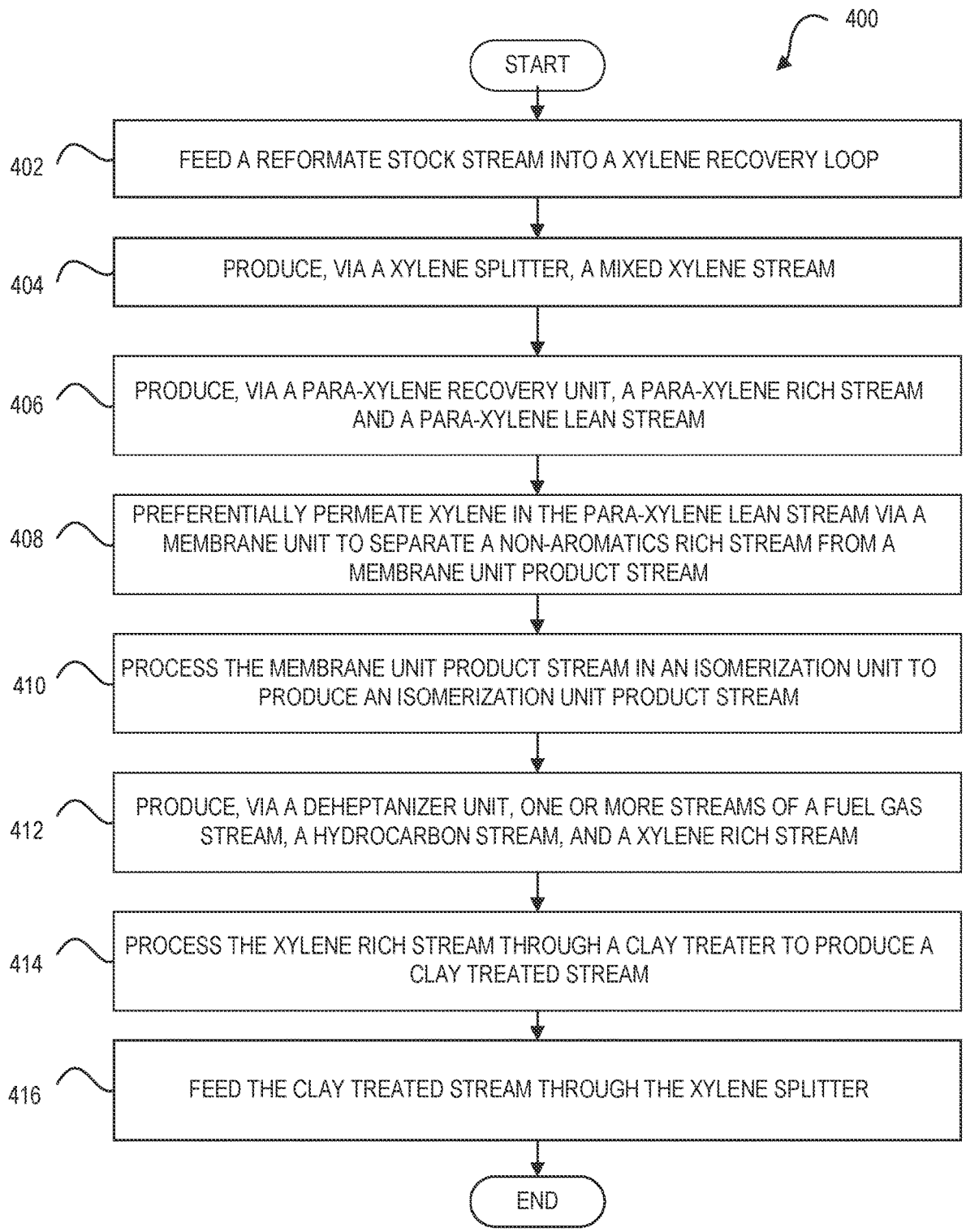
FIG. 4 is a flow chart illustrating a method for removing non-aromatic compounds from a xylene isomerization process for para-xylene production in accordance with an example embodiment, which may be used in conjunction with the system of FIG. 1 in a third configuration.

FIG. 4 illustrates a method 400 for removing non-aromatic compounds from a xylene isomerization process for para-xylene production with the membrane unit 160C in the third position. As shown in FIG. 4, the method 400 may commence at operation 402 with feeding the reformate stock stream 102 to the xylene recovery loop 101 (e.g., specifically to the xylene splitter 110). In turn, at operation 404, the xylene splitter may be configured to produce the mixed xylene stream 112 and the heavier hydrocarbon stream 114. As the mixed xylene stream 112 continues downstream to the para-xylene recovery unit 120, at operation 406, the para-xylene recovery unit 120 may be configured to produce the para-xylene lean stream 122 and the para-xylene rich stream 124. At operation 408, after the para-xylene recovery unit 120 has fed the para-xylene lean stream 122 to the membrane unit 160C, the membrane unit 160C may be configured to preferably permeate xylenes to separate the membrane unit product stream 162C from the non-aromatics rich stream 164C. At operation 410, after the membrane unit 160C has fed the membrane unit product stream 162C to the isomerization unit 130, the isomerization unit 130 may be configured to process the membrane unit product stream 162C to produce the isomerization unit product stream 132, which can then be fed to the deheptanizer unit 140. At operation 412, the deheptanizer unit 140 may be configured to produce one or more streams of the xylene rich stream 142, the fuel gas stream 144, and the hydrocarbon stream 146, and at least the xylene rich stream 142 may be fed downstream to the clay treater 150. At operation 414, the clay treater 150 may be configured to produce the clay treated stream 152, which can then be fed through the xylene splitter 110 for recirculation within the xylene recovery loop 101 at operation 416. Alternatively, the clay treated stream 152 may be output from the system 100. By separating the non-aromatics rich stream 164C, it can be removed from the system 100 without adversely impacting system efficiency or effectiveness (e.g., without having to discard streams that are more concentrated with xylenes and/or stopping operations).

Figure 5:
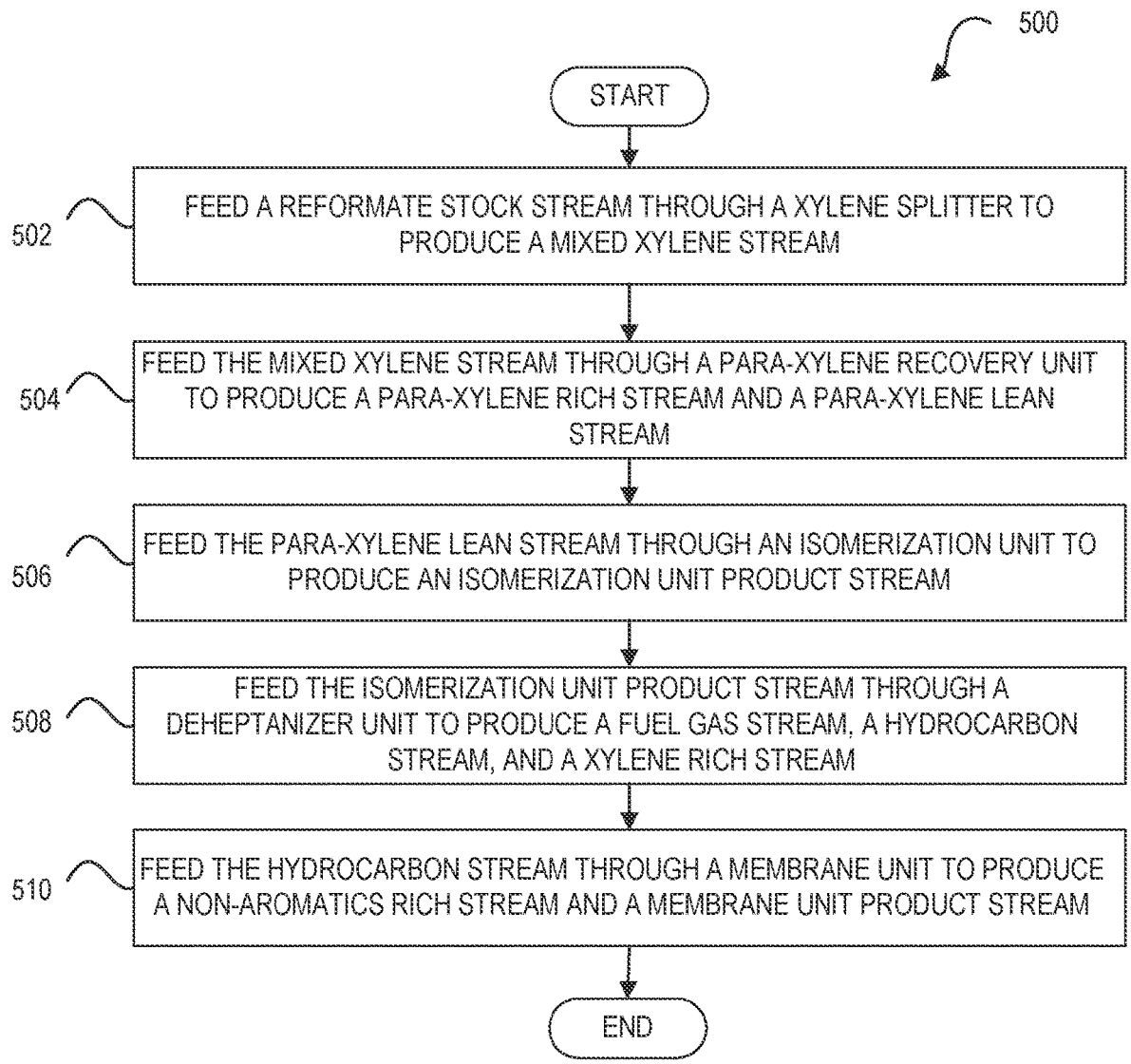
FIG. 5 is a flow chart illustrating a method for removing non-aromatic compounds from a xylene isomerization process for para-xylene production in accordance with an example embodiment, which may be used in conjunction with the system of FIG. 1 in a fourth configuration.

FIG. 5 illustrates a method 500 for removing non-aromatic compounds from a xylene isomerization process for para-xylene production. As shown in FIG. 5, the method 500 may commence at operation 502 with feeding the reformate stock stream 102 through the xylene splitter 110, which may be configured to produce the mixed xylene stream 112 and the heavier hydrocarbon stream 114. At operation 504, the xylene splitter 110 may feed the mixed xylene stream 112 to the para-xylene recovery unit 120, which may be configured to produce the para-xylene lean stream 122 and the para-xylene rich stream 124. At operation 506, the para-xylene recovery unit 120 may feed the para-xylene lean stream 122 to the isomerization unit 130, which may be configured to produce the isomerization unit product stream 132. At operation 508, the isomerization unit 130 may feed the isomerization unit product stream 132 to the deheptanizer unit 140, which may be configured to produce the xylene rich stream 142, the fuel gas stream 144, and the hydrocarbon stream 146. At operation 510, the deheptanizer unit 140 may feed the hydrocarbon stream 146 to the membrane unit 160D, which may be configured to produce the membrane unit product stream 162D and the non-aromatics rich stream 164D. At this point, the method 500 may be stopped with the output membrane unit product stream 162D being sold to another processing plant. Alternatively, although not shown, the method 500 may proceed with directing one or more of those output streams for further processing to one or more of the clay treater 150 and/or one or more additional membrane unit(s) 160D.

While the present disclosure has been described in connection with a plurality of exemplary aspects, as illustrated in the various figures and discussed above, it is understood that other similar aspects can be used, or modifications and additions can be made, to the described aspects for performing the same function of the present disclosure without deviating therefrom. For example, in various aspects of the disclosure, methods and compositions were described according to aspects of the presently disclosed subject matter. However, other equivalent methods or compositions to these described aspects are also contemplated by the teachings herein. Therefore, the present disclosure should not be limited to any single aspect, but rather construed in breadth and scope in accordance with the appended claims.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the various patent offices and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A method for removing non-aromatic compounds from a para-xylene production process, comprising:
   feeding a reformate stock stream into a xylene recycle loop comprising a xylene splitter, a para-xylene recovery unit, a membrane unit, an isomerization unit, a deheptanizer unit, and a clay treater;
   producing, via the xylene splitter configured to receive the reformate stock stream, a mixed xylene stream comprising para-xylene, ortho-xylene, and meta-xylene;
   producing, via the para-xylene recovery unit configured to receive the mixed xylene stream, a para-xylene lean stream;
   permeating xylene in the para-xylene lean stream via the membrane unit to separate a non-aromatics rich stream from a membrane unit product stream;
   processing the membrane unit product stream in the isomerization unit to produce an isomerization unit product stream;
   producing, via the deheptanizer unit configured to receive the isomerization unit product stream, a xylene rich stream;
   processing the xylene rich stream through the clay treater to produce a clay treated stream; and
   feeding the clay treated stream into the xylene splitter for recirculation within the xylene recycle loop.

2. The method of claim 1, wherein the reformate stock stream comprises non-aromatic compounds, mixed xylenes, C6 aromatic compounds, and C7 aromatic compounds.

3. The method of claim 1, wherein preferentially permeating the xylenes from the para-xylene lean stream via the membrane unit further comprises feeding the para-xylene lean stream into the membrane unit at a constant pressure between 200 to 2000 psig.

4. The method of claim 1, wherein the membrane unit comprises a one-stage membrane system.

5. The method of claim 1, wherein the membrane unit comprises a multi-stage membrane system.

6. The method of claim 1, wherein the membrane unit presents a xylene permeance of 60 $gm/m^2/hr/psi$ and a xylene to non-aromatic permeance ratio of 15.

7. The method of claim 1, further comprising producing, via the deheptanizer unit, a hydrocarbon stream.

8. The method of claim 7, wherein the isomerization unit product stream comprises 50 wt % meta-xylene, 24 wt % para-xylene, and 26 wt % ortho-xylene.

9. The method of claim 7, wherein the hydrocarbon stream comprises C6 aromatic compounds, C7 aromatic compounds, and non-aromatic compounds.

* * * * *